United States Patent
Perletti

(10) Patent No.: US 11,707,249 B2
(45) Date of Patent: Jul. 25, 2023

(54) PREDICTIVE METHOD FOR CONTROLLING A RADIOLOGICAL APPARATUS AND RADIOLOGICAL APPARATUS IMPLEMENTING IT

(71) Applicant: GENERAL MEDICAL MERATE—S.P.A., Seriate (IT)

(72) Inventor: Ivan Perletti, Carobbio degli Angeli (IT)

(73) Assignee: GENERAL MEDICAL MERATE—S.P.A., Seriate (IT)

( * ) Notice: Subject to any disclaimer, the term of this patent is extended or adjusted under 35 U.S.C. 154(b) by 98 days.

(21) Appl. No.: 17/424,349

(22) PCT Filed: Jan. 27, 2020

(86) PCT No.: PCT/IB2020/050595
§ 371 (c)(1),
(2) Date: Jul. 20, 2021

(87) PCT Pub. No.: WO2020/157623
PCT Pub. Date: Aug. 6, 2020

(65) Prior Publication Data
US 2022/0117572 A1 Apr. 21, 2022

(30) Foreign Application Priority Data
Jan. 28, 2019 (IT) .................. 102019000001225

(51) Int. Cl.
*A61B 6/00* (2006.01)
*H05G 1/44* (2006.01)

(52) U.S. Cl.
CPC ............... *A61B 6/542* (2013.01); *H05G 1/44* (2013.01)

(58) Field of Classification Search
CPC ....... A61B 6/542; A61B 6/548; A61B 6/4464; A61B 6/461; A61B 6/587; A61B 6/4452; A61B 6/4417; A61B 6/4266; A61B 6/585; A61B 6/4233; A61B 6/502; A61B 6/0414; A61B 6/488; A61B 6/465; A61B 6/586;
(Continued)

(56) References Cited

U.S. PATENT DOCUMENTS

| 6,151,383 A | 11/2000 | Xue et al. |
| 2009/0175418 A1* | 7/2009 | Sakurai ................ A61N 5/1048 378/98.5 |

(Continued)

*Primary Examiner* — Irakli Kiknadze
(74) *Attorney, Agent, or Firm* — Dickinson Wright PLLC; Andrew D. Dorisio

(57) ABSTRACT

A method for controlling a radiological apparatus through the use of: a) a control unit adapted to activate X-ray emission from an X-ray emitter of the radiological apparatus at the beginning of an exposure and deactivating X-ray emission from said X-ray emitter subsequently, and b) an X-ray transducer associated with an image detector of the radiological apparatus. Said control unit repeatedly determines a predicted value of total X-ray dose based on a signal received from said X-ray transducer, and said control unit deactivates the X-ray emission based on at least said predicted value. To determine said predicted value, said control unit repeatedly performs total X-ray dose estimates according to a model, and one or more parameters of said model are determined and modified during operation of the radiological apparatus.

13 Claims, 4 Drawing Sheets

(58) Field of Classification Search
CPC ......... A61B 6/107; A61B 6/00; A61B 6/4411; A61B 6/544; A61B 6/482; A61B 6/14; A61B 5/7275; A61B 5/4547; A61B 5/004; A61B 5/7257; A61B 6/5264; A61B 6/503; A61B 6/032; A61B 5/061; A61B 34/20; A61B 2090/376; A61B 2034/2051; A61B 6/06; A61B 6/405; A61B 6/5211; A61B 6/481; A61B 6/504; A61B 6/486; A61B 6/12; A61B 6/469; A61B 6/487; A61B 6/4441; A61B 2034/2046; A61B 6/547; A61B 5/165; A61B 5/4803; A61B 5/7267; A61B 5/7221; A61B 5/163; H05G 1/44; H05G 1/40; G01T 1/2018; G01T 1/242; G01T 1/247; G01T 1/026; G01T 1/24; H04N 5/32; H04N 5/2351; G01J 1/429; G01N 23/043; G01N 23/083; G16H 10/60; G16H 50/20; G16H 50/70; G06F 21/6254; G06F 18/2413; G06N 5/041; G06N 7/01; A61C 9/0053; G06T 7/0012; G06T 2207/30061; G06T 2207/30101; G06T 2207/20021; G06T 2207/20056; G06T 2207/10116; G06T 2207/30048; G06V 2201/031; G01B 7/003
USPC ......................................... 378/19, 62, 98.12
See application file for complete search history.

(56) References Cited

U.S. PATENT DOCUMENTS

| | | | |
|---|---|---|---|
| 2011/0054943 A1 | 3/2011 | Ohta et al. | |
| 2012/0195408 A1 | 8/2012 | Walk et al. | |
| 2013/0089247 A1* | 4/2013 | Mercuriev | G06T 5/002 382/128 |
| 2015/0139382 A1* | 5/2015 | Hyung | A61B 6/06 378/5 |
| 2015/0305823 A1* | 10/2015 | Claus | A61B 5/061 600/424 |
| 2017/0202534 A1* | 7/2017 | Crotty | A61B 6/465 |
| 2021/0307714 A1* | 10/2021 | Scott | G06T 3/4007 |

* cited by examiner

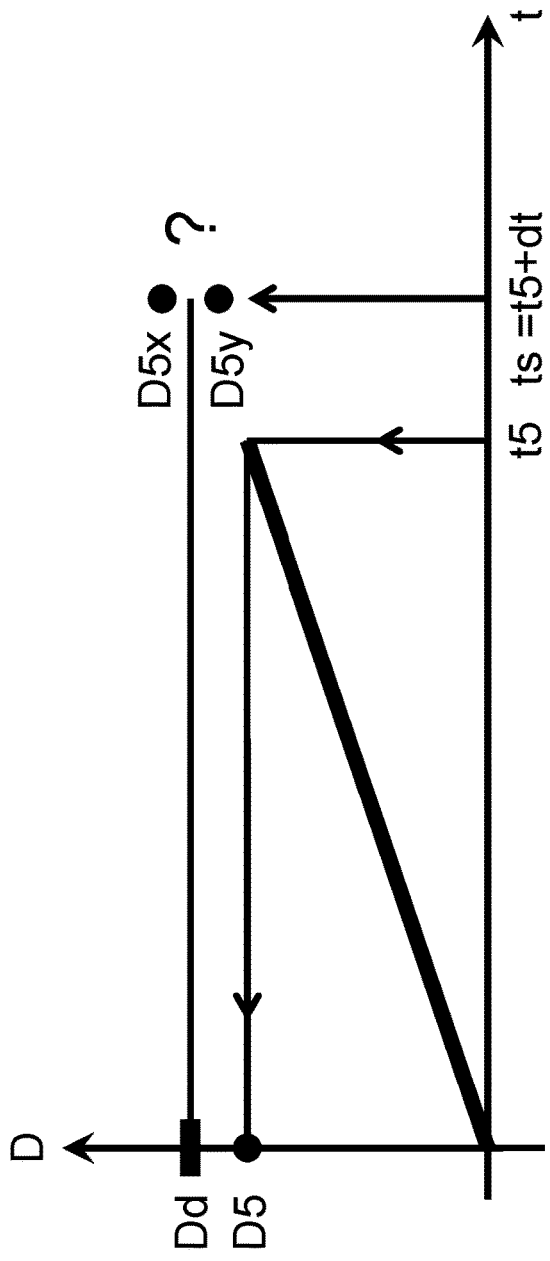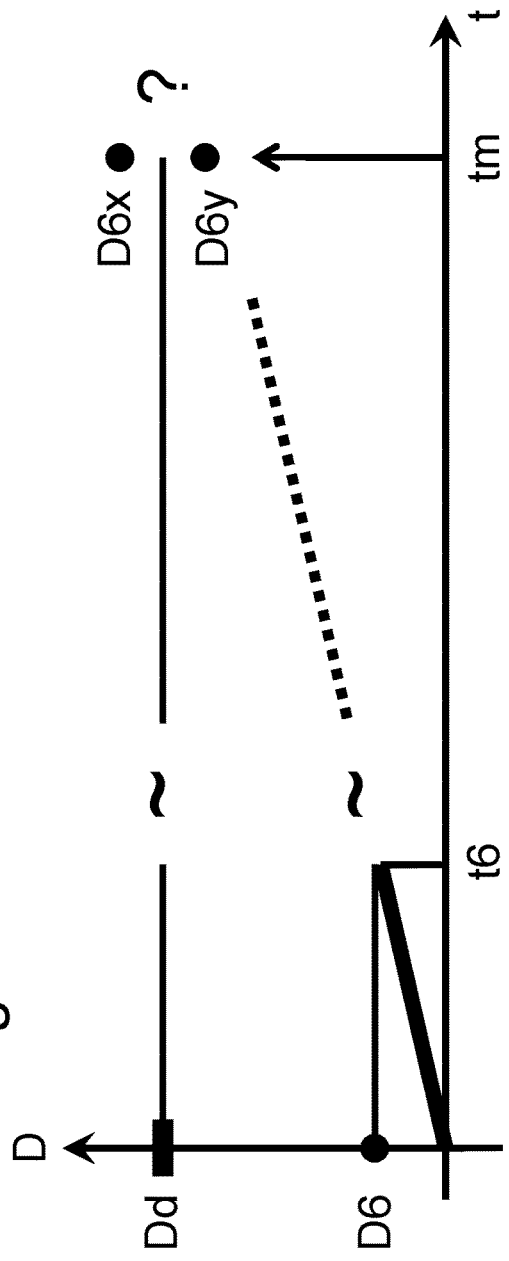

PREDICTIVE METHOD FOR CONTROLLING A RADIOLOGICAL APPARATUS AND RADIOLOGICAL APPARATUS IMPLEMENTING IT

The present disclosure is a 371 application of PCT/IB2020/050595, filed on Jan. 27, 2020, which claims priority to IT 102019000001225, filed on Jan. 28, 2019, the contents of which are incorporated by reference in their entirety.

DESCRIPTION

Field of the Invention

The present invention relates to a predictive method for controlling a radiological apparatus and a radiological apparatus implementing it.

State of the Art

Radiological apparatuses are used to obtain images by radiating with X-rays a body to be viewed. For that purpose, as is known, they are provided with an emitter of X-rays and an image detector, e.g. a plate (analog) or the combination of a scintillator (electric) and a 2D optical detector (electronic).

The exposure of the plate or of the optical detector is controlled by a control unit. U.S. Pat. No. 5,585,638 describes and illustrates an automatic exposure control system, with the initials "AEC", based on an X-ray transducer; the X-ray transducer is used to measure, in a small area, the total dose of X-rays that has crossed the body to be viewed and that has reached the optical detector.

Figure 2:
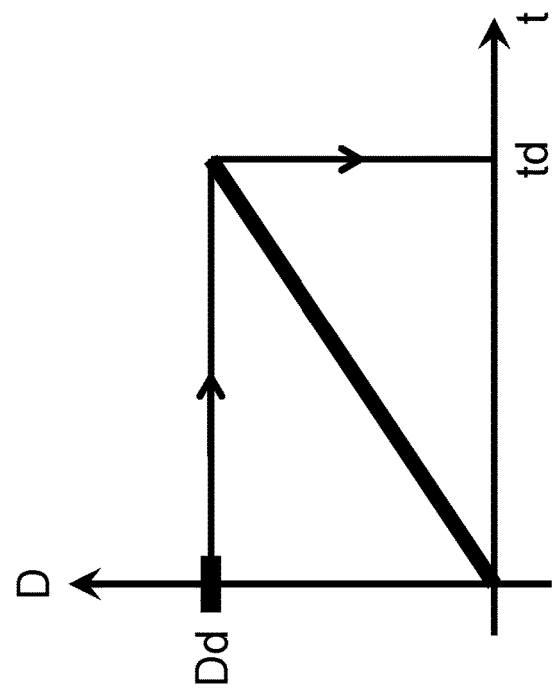

The graph of FIG. 2 helps to understand the operating principle of an AEC. The curve (which is for example and in particular a section of a straight line) indicates the total dose D measured by an X-ray transducer after the emission of X-rays has been activated by an X-ray emitter of a radiological apparatus as the time t varies. If the desired dose for obtaining a certain image of a certain body is Dd, when the curve reaches the value Dd the emission of X-rays by the X-ray emitter is deactivated (this happens at time td) and such certain image is obtained in the optical detector.

However, in practice an AEV operates in a slightly different way.

Figure 3:
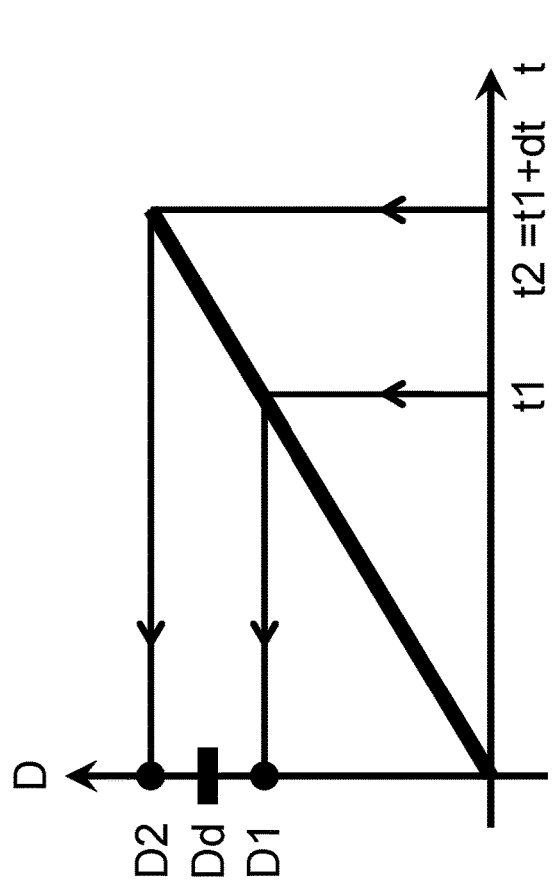

The graph of FIG. 3 helps to understand such real operation. The control unit of the radiological apparatus periodically (or almost) verifies the value measured by the X-ray transducer and, on the basis of such periodic verifications, decides when to deactivate the emission of X-rays by the X-ray emitter. At time t1, the unit reads from the transducer the value D1, compares it with the value Dd, establishes that D1 is less than Dd and therefore decides not to deactivate the emission. After a period dt, at time t2 (t2=t1+dt), the unit reads from the transducer the value D2, compares it with the value Dd, establishes that D2 is greater than Dd and therefore decides to deactivate emission. This means that the body to be viewed has received a dose of X-rays that is slightly higher than the desired one, i.e. it has been radiated for longer than necessary, but an image has however been obtained.

Figure 4:
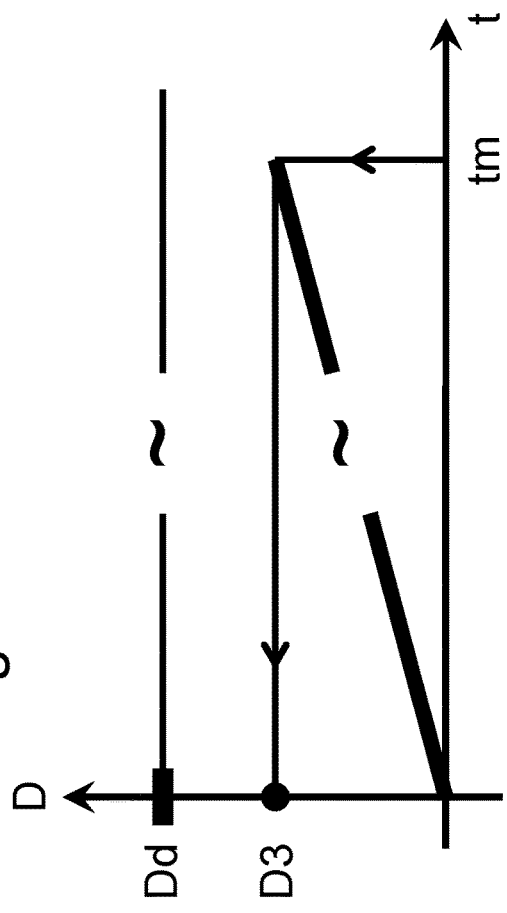

The graph of FIG. 4 helps to understand another possible undesired event.

For safety reasons, legislation envisages that exposure to X-rays for obtaining an image must not exceed a maximum time tm. Radiological apparatuses on the market respect this obligation; normally, exposure finishes much earlier; if any abnormalities occur, the AEC of the apparatus interrupts exposure at time tm and the image obtained cannot be used (it is typically very dark) and a new exposure must be performed—FIG. 4 shows the eventuality in which after time tm the total dose measured is D3 which is less than Dd. This means that the body to be viewed has been radiated for much longer than necessary, i.e. it has received a first dose of X-rays for the first exposure (which has provided an unusable image) and a second dose of X-rays for the second exposure (which has provided a usable image). Radiological apparatuses are known, which can perform estimates of the total dose of X-rays before it has been effectively radiated (completely or partly) for example from patent document US2012195408A1 and U.S. Pat. No. 6,151,383A.

SUMMARY

The general object of the present invention is to provide a method for controlling a radiological apparatus that improves the prior art, in particular that accurately prevents one or, preferably, both of the undesired events mentioned above.

It is to be noted that the solutions described and shown in the patent documents mentioned above perform estimates on the basis of a predetermined model, in particular selected during the production step of the radiological apparatus. However, such model cannot perfectly reflect the behaviour of all the various examples of apparatus produced and sold (even of the same model) especially if it is considered that the behaviour of an apparatus varies over time and is influenced for example by the ageing of the components of the apparatus and/or by phenomena and/or events that cannot be predicted a priori.

This general object and other objects are reached thanks to what is set out in the appended claims that form an integral part of the present description.

LIST OF FIGURES

Figure 1:
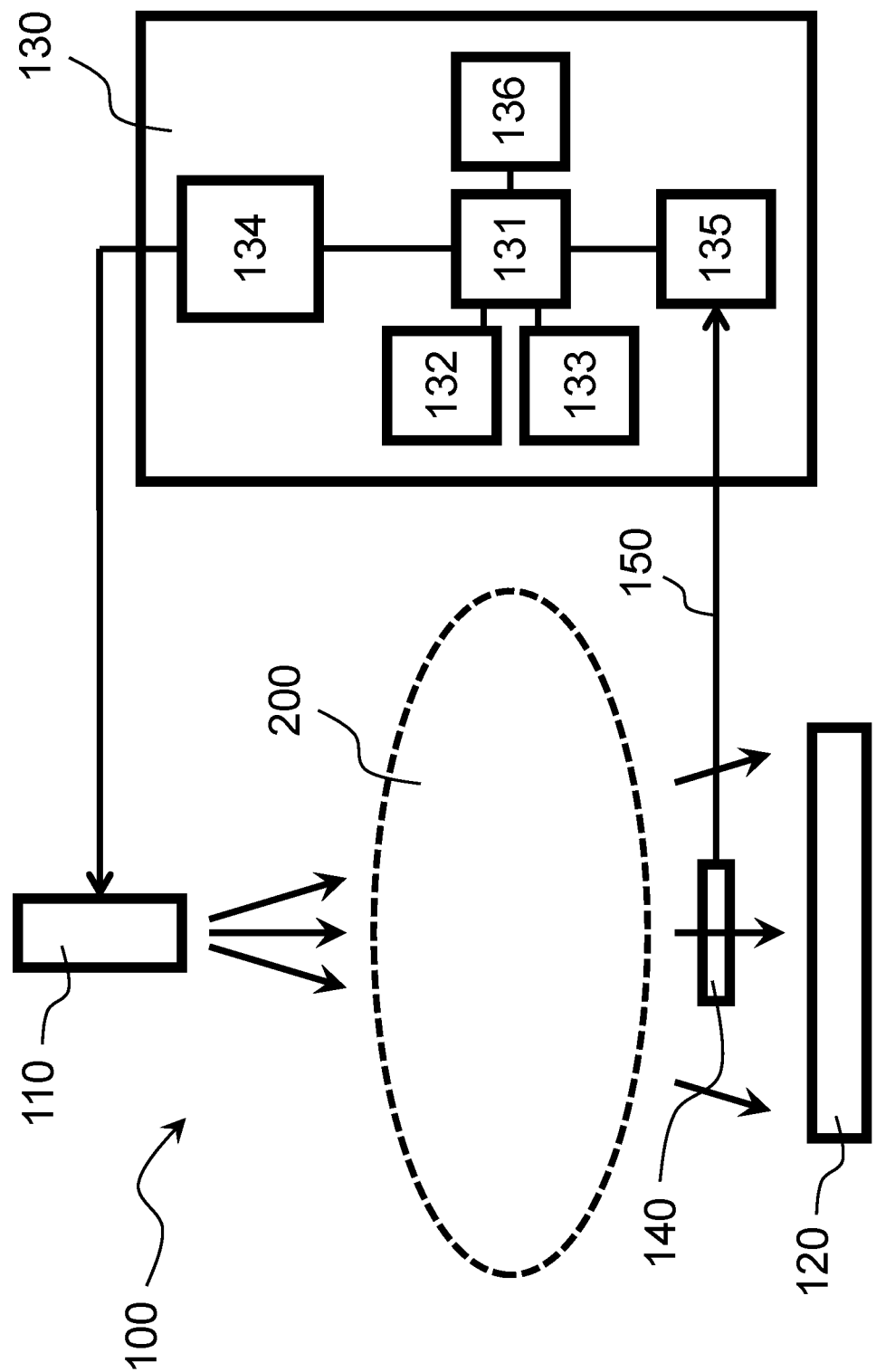
Figure 7:
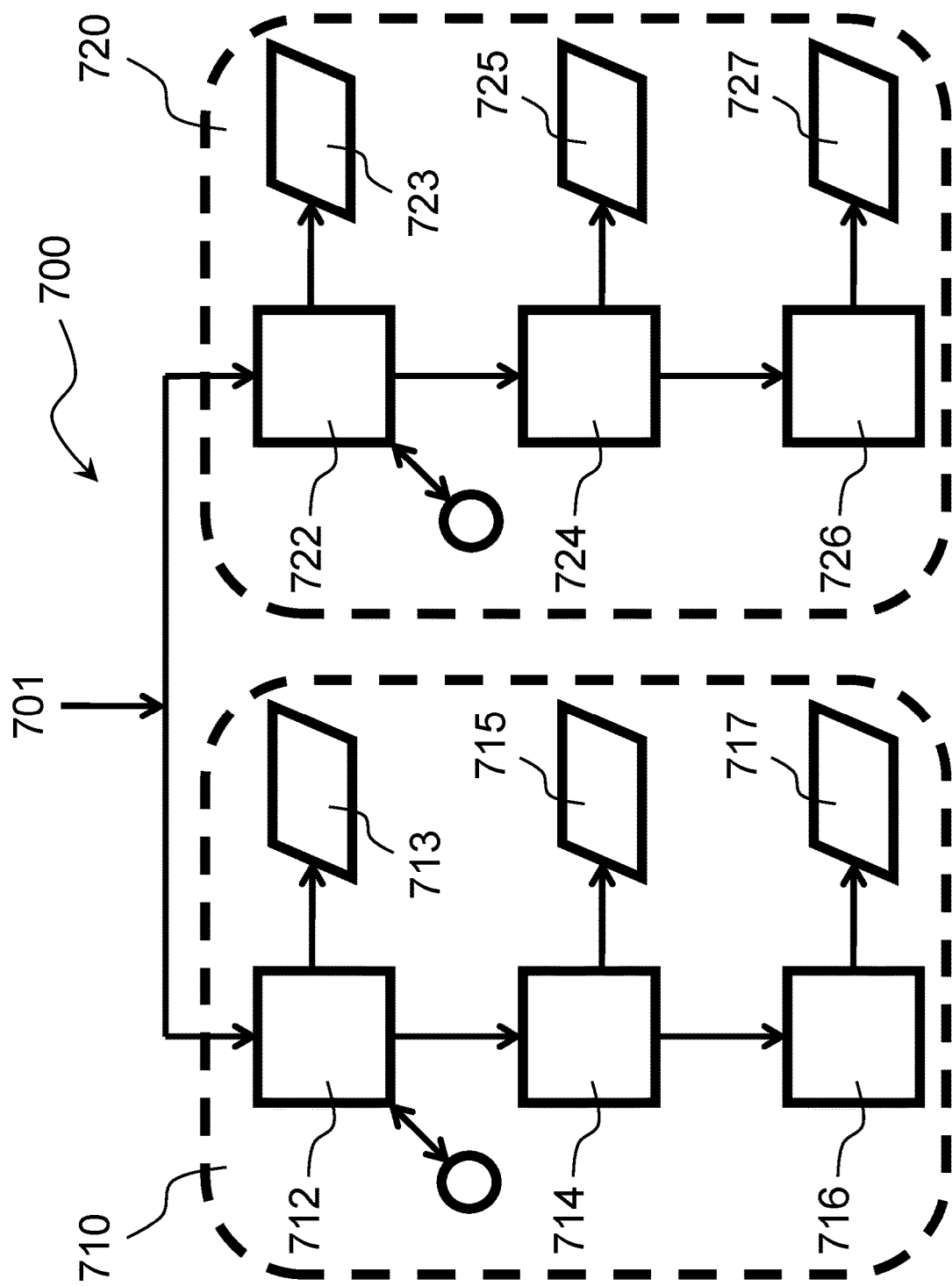

The present invention shall become more readily apparent from the detailed description that follows to be considered together with the accompanying drawings in which:

FIG. 1 shows a simplified and partial general block diagram of radiological equipment according to the present invention, FIG. 2 shows a first (idealized) graph of a total dose that illustrates the operation of an AEC according to the prior art, FIG. 3 shows a second (idealized) graph of a total dose that illustrates the operation of an AEC according to the prior art, FIG. 4 shows a third (idealized) graph of a total dose that illustrates the operation of an AEC according to the prior art, FIG. 5 shows a first (idealized) graph of a total dose that illustrates the operation of an AEC according to the present invention, FIG. 6 shows a second (idealized) graph of a total dose that illustrates the operation of an AEC according to the present invention, and FIG. 7 shows a partial flow diagram of an example of an embodiment of a control method according to the present invention.

As can be easily understood, there are various ways of practically implementing the present invention which is defined in its main advantageous aspects in the appended claims and is not limited either by the following detailed description or by the appended claims.

DETAILED DESCRIPTION

With reference to FIG. 1, a radiological apparatus 100 according to the present invention comprises for example: an X-ray emitter 110, an image detector 120 (in particular of the electronic type) and a control unit 130 connected electrically to the emitter 110 and to the detector 120; furthermore, it comprises an X-ray transducer 140 associated with the image detector 120 connected electrically to the control unit 130. FIG. 1 also shows a body 200 to be viewed. The rays emitted by the emitter 110 cross the body 200 and reach the detector 120; a part of these rays reaches (in particular crosses) the transducer 140. The control unit 130 comprises, in particular, a processor 131 associated with a program memory 132 and a data memory 133; furthermore, the unit 130 is provided with a power supply 134 that electrically powers the emitter 110, an analog-to-digital converter 135 which is electrically connected to the transducer 140, and a human-machine interface 136 which can comprise, for example, a keyboard, a screen, a mouse and a joystick. The processor 131 sends signals to the power supply 134 so as to be able to activate and deactivate (and regulate) the emission of X-rays by the emitter 110. The processor 131 receives signals from the converter 135 so as to find out/calculate the total dose of X-rays based on the dose measurement of the transducer 140.

In the example embodiment of FIG. 1, the (automatic exposure) control method performed by the unit 130 depends largely on a program stored in the memory 132; furthermore, it can also depend on data stored in the memory 133, for example, in relation to program setting data; finally, it can also depend on data entered by an operator through the interface 136; furthermore, it is not to be excluded that it can also depend on something else.

The idea at the basis of the present invention is to decide whether to interrupt the emission of X-rays by the emitter or not, not on the basis of the value of the current total dose, but on the basis of at least one predicted total dose value.

In particular, a first predicted value can be considered in order to account for the behaviour of the radiological apparatus in the short term (consider for example the first eventuality described above) and a second predicted value to account for the behaviour of the radiological apparatus in the long term (consider for example the first eventuality described above).

The prediction according to the present invention is typically in time, i.e. the predicted value is a value expected at a future time and is based on one or more values detected in a past time.

It is to be noted that if the prediction were limited to the consideration of the graphs of the figures, it would be simple; in fact, it is simple to determine any point that can be found on a straight line.

The prediction difficulty comes from some problems: the graph obtained from the electrical signal at the output from the transducer 140 is not linear but can have a different trend that is not precisely known a priori (i.e. shortly before beginning an exposure and during the exposure), the electrical signal at the output of the transducer 140 has its own intrinsic noisiness, the electrical signal at the input of the unit 130 (in particular of the converter 135) is different from the signal at the output of the transducer 140 as the electrical cable 150 that connects these two components adds noise of various kinds, it is not possible to be certain a priori (i.e. shortly before beginning an exposure and during the exposure) that everything is in the ideal conditions for the exposure (e.g. effective connection between the transducer 140 and the unit 130, state of the cable 150, . . . ).

A further general difficulty is that the prediction depends on the operation of the apparatus, and the latter changes slowly over time (in simple terms, the apparatus ("ages").

Considering FIG. 5, it can be understood that at time t5 the total measured dose is D5 less than Dd (desired dose); at this point a (first) predicted value is determined, in particular the value expected at the time ts=t5+dt; dt could for example be 10 ms; if the predicted value is D5$x$ greater than Dd, the emission of X-rays is deactivated (straight away or slightly later); if the predicted value is D5$y$ less than Dd, the emission of X-rays is not deactivated (straight away or at a slightly later time). In this way, it is certain that the limit Dd of dose absorbed by the body is not exceeded.

Considering FIG. 6, it can be understood that at time t6 the total measured dose is D6 less than Dd (desired dose); at this point a (second) predicted value is determined, in particular the value expected at the time tm (maximum exposure time); tm could for example be 500 ms; if the predicted value is D6$x$ greater than Dd, the emission of X-rays is not deactivated; if the predicted value is D6$y$ less than Dd, the emission of X-rays is deactivated (typically straight away). In this way, the exposure continues only if there is hope that it will be successful.

It is appropriate to consider that FIG. 5 and FIG. 6 typically correspond to different axis times: the time t5 is close to the end of an exposure and the time t6 is far from the end of an exposure.

It can be understood that the strategies illustrated with reference to FIG. 5 and FIG. 6 can be performed simultaneously, i.e. at every instant a short term test and a long term test can be performed. It is also possible to think about performing such two tests with a different frequency, typically the short term test very frequently (e.g. every 10 ms) and the long term test less frequently (e.g. every 100 ms).

In general (considering the example of FIG. 1 for reference purposes), the method of the present invention performs the control through the use of:

a) a control unit adapted to activate the emission of X-rays by an X-ray emitter of the radiological apparatus at the start of an exposure and to deactivate the emission of X-rays by the X-ray emitter subsequently, and b) an X-ray transducer associated with an image detector of the radiological apparatus;

the control unit repeatedly determines, preferably with a predetermined period "dt", a predicted value of total X-ray dose based on a signal received from the X-ray transducer; furthermore, the control unit deactivates the emission of X-rays at least based on the predicted value.

It is highlighted that the graphs of the figures are typically obtained by integrating the signal received from an X-ray transducer; in the example of FIG. 1, the transducer 140 measures a "accrued dose" and not a "total" dose or simply a "dose".

In order to determine the predicted value, the control unit 130 repeatedly performs total dose estimates of X-rays according to a model (or better at least one model); one or more of the parameters of the model are determined and modified during the operation of the apparatus; in practice, the model is chosen and adjusted during the production stage. Advantageously, for the determination of the estimates, in particular of the parameters of the model a Kalman filter is used.

The predicted value (calculated at a time "t") can correspond to an expected value at a subsequent time "t+dt" of total X-ray dose absorbed by the X-ray transducer starting from the beginning of the exposure; in this case, the control unit performs a comparison between the predicted value and a predetermined value (e.g. Dd in FIG. 5) and deactivates the emission of X-rays if such comparison indicates that the predicted value is greater than or equal to the predetermined value (see for example FIG. 5). In this case, the deactivation may be immediate or delayed; the maximum delay is the period "dt"; the delay may also be calculated and depend on the difference between the predetermined value and the current value.

The predicted value (calculated at a time "t") can correspond to an expected value at a subsequent predetermined time "tm" of total X-ray dose absorbed by the X-ray transducer starting from the beginning of the exposure; in this case, the control unit performs a comparison between the predicted value and a predetermined value (e.g. Dd in FIG. 6) and deactivates the emission of X-rays if such comparison indicates that the predicted value is less than the predetermined value (see for example FIG. 6). In this case, the deactivation preferably takes place immediately or as soon as the control unit establishes that the predicted value is less than the predetermined value (there will be a short delay due to the time necessary for the operations).

Typically, the "desired dose" value depends on the selection of the operator. For example, the operator chooses the anatomical part to be radiated (e.g. skull, chest, foot) and chooses the size of the patient (e.g.: S, M, L, XL); the apparatus (or better, the software of the apparatus) determines the "desired dose" on the basis of these two choices.

Typically, the "maximum time" value can depend on different factors, e.g.: the characteristics of the image detector of the apparatus, the legislation (e.g. EN 60601), the anatomical part to be radiated, the size of the patient; the first factor can be set in the apparatus during the production stage, the second factor can be integrated into the software of the apparatus, the third factor and the fourth factor can depend on the choices of the operator.

To perform the prediction of the effective dose or total dose, at least one model of the trend of the dose is created; some examples are provided below.

Considering an ideal and general mathematical model (discrete time) of ramp behaviour, which is a very simple linear model, the following is obtained:

$$x(k+1)=x(k)+dr(k)\cdot dt \quad \text{F1}$$

where $dr(k)$ is the "accrued dose" detected in the (small) time interval "dt", $x(k)$ is the sample dose value "k", and $x(k+1)$ is the subsequent sample dose value "k+1". In general, the formula F1 can be corrected by adding a term $e(k)$ to consider the effects of noise of which only the statistical characteristics are known (e.g. mean and variance) but not the punctual ones; it is difficult to overlook the noise if the aim is to work very accurately, as is the intention of the Applicant. Therefore, the following is obtained:

$$x(k+1),x(k)+dr(k)\cdot dt+e(k) \quad \text{F2}$$

The Applicant has analysed many measurements performed thereby with different powers, doses, sensors, cables, and has drawn up other formulae:

$$x(k+1)=m(k)\cdot x(k)+dr(k)\cdot dt+e(k) \quad \text{F3}$$

$$x(k+1)=x(k)+dr(k)\cdot dt+a\cdot\sin(\omega k+\phi)+e(k) \quad \text{F4}$$

$$x(k+1)=x(k)+dr(k)\cdot dt+q(t)+e(k) \quad \text{F5}$$

wherein q is for example a particular well-known electronic effect a priori which can vary over time $$x(k+1)=b\cdot x(k)+dr(k)\cdot dt+q+e(k) \quad \text{F6}$$

wherein q is for example a particular well-known electronic effect a priori which is fixed over time $$x(k+1)=m(k)\cdot x(k)+dr(k)\cdot dt+a\cdot\sin(\omega k+\phi)+e(k) \quad \text{F7}$$

$$x(k+1)=x(k)+dr(k)\cdot dt+q+a\cdot\sin(\omega k+\phi)+e(k) \quad \text{F8}$$

Therefore, there are many formulae or many possible models.

Sometimes it is possible to identify a priori only one appropriate formula; such identification can derive, for example, from experiments.

However, more generally and as can be understood better below, the Applicant has decided that it would be preferable to use simultaneously one group of (e.g. two or more) models and to perform the predictions on the basis of various models, e.g. by choosing the model that seems to fit best at a certain moment or a certain interval of time.

According to preferred embodiments, in order to determine the predicted value, the control unit repeatedly performs at least two total X-ray dose estimates according to at least two models during the operation of the apparatus and chooses (repeatedly) the estimate that it considers best as the expected value during the operation of the apparatus.

According to other preferred embodiments, in order to determine the predicted value, the control unit repeatedly performs at least two total X-ray dose estimates according to at least two models during the operation of the apparatus and (repeatedly) calculates the expected future value on the basis of at least two estimates during the operation of the apparatus; e.g. it can calculate a simple mean of two estimates or a weighted mean of two estimates.

A very effective possibility is to determine the estimates through a Kalman filter.

It is to be noted that the present invention does not exclude a model being able to be subject to adjustments during the control of the apparatus; e.g. in the formula F3, the coefficient $m(k)$ can (slightly) vary from sample to sample (or better, sample after sample, the coefficient converges or should converge towards a certain value, which is not known a priori).

Typically, the estimates are based on a known trend hypothesis of the signal received from the X-ray transducer (indicated with 140 in the example of FIG. 1).

When various estimates are used simultaneously, it is possible for a score to be assigned by the control unit to each estimate, such score representing, in particular, the quality of the estimate. The quality of the estimate can be determined, for example, by calculating the difference between the real value and the estimate.

When various models are used simultaneously, it is possible for a score to be assigned repeatedly by the control unit to each predetermined model, such score representing, in particular, the quality of the model. The quality of the model can be determined, for example, by calculating, at each sampling time, the difference between the real value and the value provided by the model and then adding together such differences; the model having such lower sum can be considered the best model.

If the score of all the models (at a certain time) is less than a minimum value, it may be envisaged that the control unit signals an abnormal operating condition so that, for example, an intervention can be arranged on the apparatus. The signal may be acoustic and intended for example for an operator and/or visual and intended for example for an operator or can consist simply of the storage of such abnormal operation condition in an appropriate memory and/or sending information so that such abnormal operating condition crosses any transmission means.

If the score of all the models is less than a minimum value for a predetermined time interval, it may be envisaged that the control unit signals an abnormal operating condition so that, for example, an intervention can be arranged on the apparatus.

The signal may be acoustic and intended for example for an operator and/or visual and intended for example for an operator or can consist simply of the storage of such abnormal operation condition in an appropriate memory and/or sending information so that such abnormal operating condition crosses any transmission means.

The methods described above are particularly suitable to be implemented by a computerized control unit such as, for example, the unit 130 of FIG. 1. The method envisages repeating a series of operations. Typically, such repetition takes place with a "predetermined period", e.g. 10-20 ms; however, such "predetermined period" is not to be considered very rigorous, therefore variations of 10% or 20% are perfectly tolerable.

FIG. 7 shows a partial flow diagram 700 of an embodiment of a control method according to the present invention, which uses two models; the diagram 700 can be considered a part of a complete diagram that corresponds to a "computer program" or simply "program"; the rectangular blocks of the diagram correspond to portions of code.

A value 701 measured at time "t" by the transducer 140 is provided as a input to the two models, a first model 710 and a second model 720, which correspond in particular to two "procedures" or "functions" of the "program".

In relation to the first model 710, at the step 712 the score of the model itself is updated (which is an index of the quality of the model) in light of the value 701 and provides it as an output 713, at the step 714, the expected value at time "t+dt" is calculated by the first model also on the basis (not necessarily only) of the value 701 and provides it as an output 715, at step 716, the expected value is calculated by the first model at time "tm" also on the basis (not necessarily only) of the value 701 and it is provided as an output 717.

In relation to the second model 720, at the step 722 the score of the model itself is updated (which is an index of the quality of the model) in light of the value 701 and provides it as an output 723, at the step 724, the expected value is calculated by the second model at time "t+dt" also on the basis (not necessarily only) of the value 701 and provides it as an output 725, at step 726, the expected value is calculated by the second model at time "tm" also on the basis (not necessarily only) of the value 701 and it is provided as an output 727.

The terms "input" and "output" were previously used with reference to "procedure" or "functions" of a "program" and not with reference to a human-machine interface, e.g. the interface 136.

On the basis of the values 713, 715, 717, 723, 725, 727, the control unit 130 can make the choice as to whether to deactivate the emission of X-rays by the emitter 110 or not; the simplest and most effective solution (but not the only possible one) is to use for the choice the results of the model having the highest score on an individual basis.

From the above, it is clear that an apparatus with an exposure regulation system according to the present invention is very advantageous. In fact, it does not require any complicated calibration as the system is self-regulating.

Furthermore, the system allows at the same time the signal to be filtered from any noise and abnormal conditions to be identified both in the short term and in the long term.

The invention claimed is:

1. A method for controlling a radiological apparatus through the use of:
   a) a control unit configured to activate X-ray emission from an X-ray emitter of the radiological apparatus at the beginning of an exposure and deactivating X-ray emission from said X-ray emitter subsequently, and
   b) an X-ray transducer associated with an image detector of the radiological apparatus;
   wherein said control unit repeatedly determines, a predicted value of total X-ray dose based on a signal received from said X-ray transducer, and
   wherein said control unit deactivates the X-ray emission based on at least said predicted value;
   wherein in order to determine said predicted value, said control unit repeatedly performs total X-ray dose estimates according to a model,
   wherein one or more parameters of said model are determined and modified during operation of the radiological apparatus,
   wherein said predicted value is calculated at a time "t" and corresponds to an expected value at a predetermined subsequent time "tm" of total X-ray dose absorbed by said X-ray transducer starting from the beginning of said exposure, and wherein said control unit makes a comparison between said predicted value and a predetermined value and deactivates X-ray emission if said comparison indicates that said predicted value is lower to said predetermined value;
   wherein the predetermined subsequent time "tm" is a maximum exposure time according to legislation.

2. The method according to claim 1, wherein said control unit deactivates the X-ray emission after having carried out said comparison.

3. The method according to claim 1, wherein in order to determine said predicted value, said control unit repeatedly performs at least two total X-ray dose estimates according to at least two models and chooses the estimate that considers better as expected future value.

4. The method according to claim 3, wherein said estimates are based on a known trend hypothesis of said signal received from said X-ray transducer.

5. The method according to claim 3, wherein a score is assigned to each determined estimate by said control unit.

6. The method according to claim 3, wherein a score is assigned to each predetermined model repeatedly by said control unit.

7. The method according to claim 6, wherein if the score of all the models is lower than a minimum value, said control unit signals an anomalous operating condition.

8. The method according to claim 6, wherein if the score of all the models is lower than a minimum value for a predetermined time interval, said control unit signals an anomalous operating condition.

9. The method according to claim 1, wherein in order to determine said predicted value, said control unit repeatedly performs at least two total X-ray dose estimates according to at least two models and calculates the expected future value on the basis of at least two estimates.

10. The method according to claim 1, wherein said estimates are determined through a Kalman filter.

11. A radiological apparatus with an X-ray emitter and an image detector (120), the apparatus comprising:

a) a control unit configured to activate X-ray emission from said X-ray emitter at the beginning of an exposure and deactivate X-ray emission from said X-ray emitter subsequently, and b) an X-ray transducer associated with said image detector and electrically connected to said control unit, wherein said control unit is arranged to carry out the method according to claim 1.

12. The radiological apparatus according to claim 11, wherein said control unit has a computer program which comprises one or more code portions configured to carry out the operations of the method according to claim 1.

13. A method for controlling a radiological apparatus through the use of:

a) a control unit configured to activate X-ray emission from an X-ray emitter of the radiological apparatus at the beginning of an exposure and deactivating X-ray emission from said X-ray emitter subsequently, and b) an X-ray transducer associated with an image detector of the radiological apparatus;

wherein said control unit repeatedly determines, a predicted value of total X-ray dose based on a signal received from said X-ray transducer, and wherein said control unit deactivates the X-ray emission based on at least said predicted value;

wherein in order to determine said predicted value, said control unit repeatedly performs total X-ray dose estimates according to a model, said estimates are determined through a Kalman filter, wherein one or more parameters of said model are determined and modified during operation of the radiological apparatus.

* * * * *